United States Patent [19]

Leonidov et al.

[11] Patent Number: 5,543,147
[45] Date of Patent: Aug. 6, 1996

[54] CRYSTALLINE MODIFICATION OF 2,4-DIOXO-6-METHYL-1,2,3,4-TETRAHYDROPYRIMIDINE, A METHOD FOR THE PREPARATION THEREOF AND A MEDICINAL PREPARATION BASED ON IT

[75] Inventors: Nikolai B. Leonidov, ulitsa Zatonnaya, 12, Korpus 1, Kv. 158, Moscow; Nikolai G. Selezenev, Ryazan, both of Russian Federation

[73] Assignee: Nikolai B. Leonidov, Russian Federation

[21] Appl. No.: 307,654

[22] PCT Filed: Jan. 20, 1993

[86] PCT No.: PCT/RU93/00018

§ 371 Date: Nov. 17, 1994

§ 102(e) Date: Nov. 17, 1994

[87] PCT Pub. No.: WO94/17046

PCT Pub. Date: Aug. 4, 1994

[51] Int. Cl.$^6$ .................................................. A61L 15/16
[52] U.S. Cl. .................. 424/400; 424/444; 544/309; 514/269; 514/270
[58] Field of Search .............................. 424/400, 195.1; 514/212, 269, 270; 544/309

[56] References Cited

U.S. PATENT DOCUMENTS 4,986,985  1/1991  Grossman et al. .................. 424/195.1
5,162,316  11/1992  Coates .................................... 514/212

FOREIGN PATENT DOCUMENTS 0306185  3/1989  European Pat. Off. .
3513391  12/1985  Germany .
101690   7/1952  Russian Federation .
194096   5/1967  Russian Federation .

OTHER PUBLICATIONS

Mashkovsky, M. D. "Lekarstvennye sredstva". posobie po farmakoterapii dlya vrachei, 1986, izdanie desyate, tom 2, izd. Meditsina M., pp. 138–139.

Primary Examiner—Thurman K. Page
Assistant Examiner—William E. Benston, Jr.
Attorney, Agent, or Firm—Ladas & Parry

[57] ABSTRACT

A crystalline modification of 2,4-dioxo-6-methyl-1,2,3,4-tetrahydropyrimidine prepared by cooling a solution of 2,4-dioxo-6-methyl-1,2,3,4-tetrahydropyrimidine in water, an organic solvent or in a mixture thereof with a cooling agent at a rate not below 6° C./min to crystallization followed by separation of the obtained crystals and drying them. The crystalline modification has high antiinflammatory and wound-healing activity and is an active substance in medicaments used for treatment of burns and wounds of various organs.

14 Claims, No Drawings

CRYSTALLINE MODIFICATION OF 2,4-DIOXO-6-METHYL-1,2,3,4-TETRAHYDROPYRIMIDINE, A METHOD FOR THE PREPARATION THEREOF AND A MEDICINAL PREPARATION BASED ON IT

FIELD OF TECHNOLOGY

The present invention pertains to organic chemistry or, more exactly to a new crystalline modification of 2,4-dioxo-6-methyl-1,2,3,4-tetrahydropyrimidine, a method for the preparation thereof, and a medicinal preparation based on it.

PRIOR ART

There is a known crystalline form of 2,4-dioxo-6-methyl-1,2,3,4-tetrahydropyrimidine (SU, A, 194096) characterized by the following set of values of interplane spacings d and relative intensities of reflexes I:

| d, Å | I |
|---|---|
| 8.005 | 17 |
| 5.497 | 9 |
| 5.315 | 100 |
| 4.105 | 4 |
| 4.004 | 2 |
| 3.648 | 38 |
| 3.411 | 16 |
| 3.332 | 3 |
| 3.169 | 23 |
| 3.110 | 4 |
| 2.805 | 3 |
| 2.723 | 1 |
| 2.667 | 3 |
| 2.613 | 3 |
| 2.569 | 27 |
| 2.469 | 1 |
| 2.382 | 1 |
| 2.340 | 1 |
| 2.275 | 11 |
| 1.929 | 3 |
| 1.867 | 1 |
| 1.828 | 2 |
| 1.712 | 5 |
| 1.640 | 1 |
| 1.599 | 1 |
| 1.588 | 1 |

The said crystalline form of 2,4-dioxo-6-methyl-1,2,3,4-tetrahydropyrimidine is prepared by crystallization of the said compound out of its aqueous solution. The resulting product is a white crystalline powder poorly soluble in water and ethyl alcohol, insoluble in ether, chloroform, characterized by the above-described values of interplane spacings d and relative intensities of reflexes I. This compound posessing the antiinflammatory and wound healing effect is characterized by insufficiently high effectiveness, toxicity, and induction of side effects.

The said compound finds an application as the active substance of a medicinal preparation for treatment of wounds, burns, bone fractures, X-ray disease, leukopenia, gastric and duodenal ulcer, hepatitis, pancreatitis and others (M. D. Mashkovsky, Pharmaceuticals, 1984, Medizina Publishers, Moscow, v. 2, p. 138).

For instance, there is a known pharmaceutical containing the said compound as the active substance used for treatment of pure postoperation wounds by the intramuscular or oral routes (G. L. Bilich—Stimulation of regeneration and defence mechanisms in infantile surgery, 1976, Medizina Publishers, Moscow, p. 31–32).

The intramuscular inoculation of the drug facilitates the spread of the greater part of the drug in other tissues and organs as a result of which no necessary topical concentration of the drug is achieved reculting in no efficacy of the treatment.

After oral administration of the drug part of it is destroyed in the stomach and no necessary concentration of the drug in the area of the wound is achieved either. This does not create a sufficient wound-healing effect of the drug and prolongs the period of treatment.

There is known pharmaceutical containing as the active substance the saif compound in the form of 5–10% liniment for topical treatment of wounds (M. D. Mashkovsky, Pharmaceuticals, 1984, Medizina Publishers, Moscow, v. 2, p. 48–60). The said drug does not accelerate the wound healing greatly (by 19.4%) and is not highly effective in treatment of suppurating wound.

Also known is an eye ointment containing the said compound as the active substance (E. A. Egorov, Application of methyluracil in ophthalmology, 1968, Kazan Medical Journal, No. 4, p. 71–72).

The said eye ointment is used for treatment of different kinds of eye cornea wounds. The use of this ointment facilitates wound healing, however, in severe forms of burns against the background of treatment there appears cicatricial tissue impairing the vision, there also frequently occur cases of secondary infection and inflammatory processes.

The said eye ointment was tested only experimentally in animals but not clinically in human patients.

The claimed crystalline modification of 2,4-dioxo-6-methyl-1,2,3,4-tetrahydropyrimidine, the method for its production and use are novel and have not been described in the literature.

DISCLOSURE OF THE INVENTION

The invention was aimed at the creation of a new crystalline modification of 2,4-dioxo-6-methyl-1,2,3,4-tetrahydropyrimidine possessing high antiinflammatory and wound-healing activity, the development of a method for production of this modification and a pharmaceutical based thereon possessing a high therapeutic efficacy, low toxicity, causing no side effects, and shortening the period of treatment when used in lower dosages.

This task has been achieved by the claimed new crystalline modification of 2,4-dioxo-6-methyl-1,2,3,4-tetrahydropyrimidine characterized, according to the invention by the following interplane spacings d and relative intensity of reflexes I:

| d, Å | I |
|---|---|
| 9.668 | 9 |
| 6.592 | 100 |
| 4.838 | 36 |
| 3.843 | 5 |
| 3.625 | 7 |
| 3.431 | 20 |
| 3.248 | 48 |
| 2.916 | 8 |
| 2.799 | 9 |
| 2.479 | 4 |
| 2.429 | 7 |
| 2.405 | 6 |
| 2.292 | 8 |
| 2.043 | 4 |
| 1.699 | 3 |

The new crystalline modification of 2,4-dioxo-6-methyl-1,2,3,4-tetrahydropyrimidine is characterized by a higher antiinflammatory and wound-healing activity as compared with the known crystalline form of this substance, by lower toxicity and fewer side effects.

The invention is also the method for production of the new crystalline modification of the said compound which, according to the invention, consists in that a solution of 2,4-dioxo-6-methyl-1,2,3,4-tetrahydropyrimidine in water or an organic solvent or a mixture thereof is cooled with a cooling agent at a rate not below 6° C./min to its complete crystallization followed by separation of the resulting crystals and drying thereof. In doing so, ethanol is expediently used as a solvent, and liquid nitrogen or carbon dioxide as a cooling agent. Drying is preferably done by vacuumization at a pressure not below $10^{-2}$ mm Hg. The resulting crystalline modification has a high antiinflammatory and wound-healing activity and finds application in medicine. The claimed pharmaceutical with the antiinflammatory and wound-healing effect containing the active substance and a pharmaceutically acceptable diluent, according to the invention, contains a crystalline modification of 2,4-dioxo-6-methyl-1,2,3,4-tetrahydropyrimidine as the active substance.

The claimed pharmaceutical may be used in any pharmaceutically acceptable medicinal form (powder, ointment, liniment, suspension, suppository, and others).

The claimed pharmaceutical in the suspension form preferably contains 1.0–2.5% by weight of the active substance, and 0.9% aqueous solution of sodium chloride or doubly-distilled water as the pharmaceutical diluent.

The claimed preparation as a liniment preferably contains 4–6% by weight of the active substance and castor oil as the pharmaceutical diluent.

The claimed preparation in the form of an ointment preferably contains 1.0–2.5% by weight of the active substance and an ointment base consisting of a mixture of lanoline and vaseline at a ratio of 1.0:1.0–2.5, respectively, as the pharmaceutical diluent.

The claimed pharmaceutical, according to the invention, may consist of the active substance—the claimed crystalline modification of 2,4-dioxo-6-methyl-1,2,3,4-tetrahydropyrimidine in combination with para-aminobenzol-sulphamid at the following ratio of components in % by weight:

| | |
|---|---|
| crystalline modification of 2,4-dioxo--6-methyl-1,2,3,4-tetrahydropyrimidine | 45–55, |
| para-aminobenzolsulphamid | 45–55. |

The claimed pharmaceutical, as compared with the known preparation exhibits a higher antiinflammatory and wound-healing activity which permits to decrease its dosage considerably and to eliminate side effects. The higher therapeutic efficacy of the claimed preparation permits to shorten the time of treatment (because of the more rapid healing of both linear and plane wounds). The claimed preparation may be used in new medicinal forms (liniment and suspension) which had been beyond realization when the preparation had been prepared on the basis of the known crystalline form of the said substance. The claimed preparation in the form of liniment possesses a high regenerating, antiinflammatory and wound-healing activity, decreases exudative-alternative changes in the focus of lesion, prevents excessive formation and proliferation of the connective tissue and scarring.

The claimed liniment possesses bioaccessibility exceeding 30-fold that of the ointment based on the known crystalline form of the said compound. The claimed preparation in the form of a suspension has a high antiinflammatory and wound-healing activity and prolonging effect and finds application in healing of burns and wounds of different origins. The claimed preparation in the form of an ointmentis applied for treatment of burns and wounds of different origins, in particular, in the field of ophthalmology for treatment of burns and wound lesions of the eyes. In this, the claimed preparation reduces the inflammatory reaction of the eye tissues and prevents secondary infections in burns and wounds of the eyes, facilitates epithelization of the eye cornea in burns and wounds. The claimed preparation containing the crystalline modification of the said compound in combination with para-aminobenzolsulphamid has a high wound-healing activity in poorly healing infected wounds (trophic ulcers of venous origin, postoperational suppurating wounds). The time of healing with the application of the claimed preparation is reduced 2-fold as compared with that observed in the use of known preparations.

THE BEST VARIANT OF THE INVENTION EMBODIMENT

The claimed new crystalline modification of 2,4-dioxo-6-methyl-1,2,3,4-tetrahydropyrimidine is a white powder with high fluidity, no smell, poorly soluble in water and ethyl alcohol, practically insoluble in ethyl ther and chloroform.

The methods using qualitative and quantitative determinations established that the claimed substance is 2,4-dioxo-6-methyl-1,2,3,4-tetrahydropyrimidine with the purity of 99.8%. These data were confirmed by the method of NMR$^{13}$C spectroscopy of high resolution which was carried out in an NMR-spectrometer XL-400 of VAPIAN Company with the rate of observation for $^{13}$C nuclei of 100 MHz. The measurements of chemical shifts of $^{13}$C nuclei in samples of the claimed crystalline modification of the compound and the known crystalline form of this compound were carried out for their saturated solutions in deuterated dimethylsulfoxide with the accuracy of 0.1 ppm. The values of chemical shifts are presented in Table 1.

TABLE 1

Chemical shifts of $^{13}$C carbon nuclei of the claimed crystalline modification of 2,4-dioxo-6-methyl-1,2,3,4-tetrahydropyrimidine and the known crystalline form of this compound, ppm*.

Position of carbon atom in the molecule of 2,4-dioxo-6-methyl-1,2,3,4-tetrahydropyrimidine

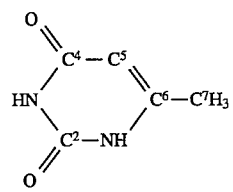

| Compound | $C^2$ | $C^4$ | $C^5$ | $C^6$ | $C^7$ |
|---|---|---|---|---|---|
| The claimed compound (a new crystalline modification) | 151.4 | 163.9 | 98.6 | 152.7 | 18.3 |
| The known compound | 151.5 | 164.1 | 98.8 | 152.9 | 18.4 |

*The chemical shifts of NMR$^{13}$C were measured with the accuracy of $10^{-1}$ ppm. in relation to the signal of dimethylsulfoxide solvent ($\delta_{tms} = 39.56$ ppm.) and recalculated into the TMS-scale (THS-tetramethylsilane Si(CH$_3$)$_4$).

The analysis of NMR$^{13}$C spectra of the compared specimens of the said compound shows that at the selected regime of spectroscopy the spectra of all specimens had no admixtures at the level of the signal/noise ratio=500. The results presented in Table 1 demonstrate that the claimed crystalline modification of 2,4-dioxo-6-methyl-1,2,3,4-tetrahydropyrimidine is an individual compound identical with the known compound in the chemical structure and purity.

Diffractometric roentgenophase analysis was used for identification of the crystalline structures of the compared specimens of the new crystalline modification and the known form of the said compound. Roentgenograms of the said analysed specimens were obtained in diffractometer DRON-2.0 with $\lambda$ Cu-k$_\alpha$ radiation. The values of interplane spacings and relative intensities of reflexes are presented in Table 2.

TABLE 2

Interplane spacings d and relative intersities of reflexes I of the known crystalline form and the new crystalline modification of 2,4-dioxo-6-methyl-1,2,3,4-tetrahydropyrimidine

| The known crystalline form of the said compound | | The new crystalline modification of the said compound | |
|---|---|---|---|
| I | d, Å | I | d, Å |
| 1 | 2 | 3 | 4 |
| 17 | 8.005 | 9 | 9.668 |
| 9 | 5.497 | 100 | 6.592 |
| 100 | 5.315 | 36 | 4.838 |
| 4 | 4.105 | 5 | 3.843 |
| 2 | 4.004 | 7 | 3.625 |
| 38 | 3.648 | 20 | 3.431 |
| 16 | 3.411 | 48 | 3.248 |
| 3 | 3.332 | 8 | 2.916 |
| 23 | 3.169 | 9 | 2.799 |
| 4 | 3.110 | 4 | 2.479 |
| 3 | 2.805 | 7 | 2.429 |
| 1 | 2.723 | 6 | 2.405 |
| 3 | 2.667 | 8 | 2.292 |
| 27 | 2.569 | 3 | 1.699 |
| 1 | 2.469 | | |
| 1 | 2.382 | | |
| 1 | 2.340 | | |
| 11 | 2.275 | | |
| 3 | 1.929 | | |
| 1 | 1.867 | | |
| 2 | 1.828 | | |
| 5 | 1.712 | | |
| 1 | 1.640 | | |
| 1 | 1.599 | | |
| 1 | 1.588 | | |

A comparison of the data presented in Table 2 shows the claimed crystalline modification to be an individual crystalline form of the said compound differing from the known crystalline form of this compound.

The absorption spectra of the claimed crystalline modification of 2,4-dioxo-6-methyl-1,2,3,4-tetrahydropyrimidine in water, ethyl alcohol (96%) and 0.1 mol/l sodium hydroxide solution were studied in the range from 200 nm to 300 nm. It was established that the absorption spectra in all the said solvents were characterized by two absorption bands with maxima about 204 nm and 260 nm (water, ethyl alcohol) and about 217 nm and 275 nm (0.1 mol/l sodium hydroxide solution). Here the spectra of the claimed compound and the known one differ insignificantly.

The tests carried out by infra-red spectroscopy revealed the differences of the claimed crystalline modification from the known crystalline form of the said compound. In the IR-spectrum of the known crystalline form in the area of deformation oscillations of C—H and N—H bonds (800–900 cm$^{-1}$) there was a wide unresolved band at 830–900 cm$^{-1}$, while in the IR-spectrum of the new crystalline modification in this area there were two well-resolved absorption bands about 870 cm$^{-1}$ and 822 cm$^{-1}$ as well as a very weak band about 840 cm$^{-1}$.

Thus, the above data attest to the claimed compound to be a new crystalline modification of 2,4-dioxo-6-methyl-1,2,3,4-tetrahydropyrimidine.

The claimed crystalline modification of 2,4-dioxo-6-methyl-1,2,3,4-tetrahydropyrimidine exhibits high antiinflammatory and wound-healing activities. These activities of the claimed compound were compared with the wound-healing activity of the known compound in experimental animals.

The tests were carried out in 2 groups of 41 random-bred white male rats weighing 200±10 g. The experimental model in the 1st group were linear wounds of 50 mm long inflicted on the backs of the rats. Depending on the crystalline form of the tested compound used the rats were divided into 3 series. The first series was control—the wounds were pricked once daily with 0.9% aqueous solution of sodium chloride (0.5 ml) for 3 days. In the 2nd series the wounds were pricked by the same method with 1% solution of the known crystalline form of the said compound in 0.9% aqueous solution of sodium chloride. In the 3rd series the wounds were pricked by the same method with 0.25% solution of the claimed compound in 0.9% aqueous solution of sodium chloride.

The choice of concentrations of solutions of the compared crystalline forms of the said compound was based on preliminary experiments which had shown that a significant wound-healing effect of the known crystalline form of the said compound was manifested after the use of its solution with a concentration 1% by weight, whereas a comparable wound-healing effect of the claimed modification of the said compound was manifested after the use of its solution in a concentration of 0.25% by weight. Based on these data, statistically significant differences in the wound-healing activity of the compared crystalline forms of the said compound were confirmed when they were used in solutions with concentrations of 1% by weight and 0.25% by weight, respectively. The results of the study are presented in Table 3.

TABLE 3

The results of comparative assessment of the wound-healing activity of the claimed modification and the known crystalline form of the said compound using a model of linear wounds

| Series No. | No. of animals | Strength of the scar, g/mm$^2$ | Increase of the scar strength as compared with control |
|---|---|---|---|
| 1<br>0.9% aqueous solution of NaCl - control | 7 | 30.1 ± 1.3 | — |
| 2<br>1% solution of the known form of the compound in 0.9% aqueous solution of NaCl | 7 | 40.1 ± 5.0 | 33.2 |
| 3<br>0.25% solution of claimed modification of the compound in 0.9% aqueous solution of NaCl | 7 | 57.3 ± 9.0 | 90.4 |

Plane multilayer wounds of 400 mm$^2$ in area inflicted on the backs of rats were an experimental model in the 2nd group of experiments. The animals were also divided into 3 series. Here, the pricking of the wound was done by the same schedule as in the 1st group. The parameters of the wound process in the time course at 7, 10 and 15 days after wound inflicting were assessed by the methods of tensiometry, planimetry and clinical observations. The time of falling off of crusts and complete healing of the wounds was determined. The rate of the wound area decrease (V) in the course of healing was calculated by the formula $$V = \frac{S_o - S_t}{S_o} \cdot 100,$$

wherein $S_o$ is the initial wound area, mm$^2$, $S_t$ the wound area on the day of measurement t, mm$^2$.

The results of trials of the wound-healing activity of the claimed and the known crystalline forms of the said compound were statistically treated with the confidence limit of 95%. The experimental results are presented in Tables 4 and 5.

TABLE 4

The results of comparative assessment of the rate of plane wounds healing after the use of the claimed modification and the known crystalline form of the said compound

| Series No. | No. of animals | Rate of healing at days, % | | |
|---|---|---|---|---|
| | | 7 | 10 | 15 |
| 1<br>0.9% aqueous solution of NaCl - control | 6 | 56.4 ± 5.9 | 58.2 ± 5.4 | 74.8 ± 5.4 |
| 2<br>1% solution of the known form of the compound in 0.9% aqueous solution of NaCl | 7 | 57.5 ± 8.3 | 80.2 ± 2.0 | 90.2 ± 2.8 |
| 3<br>0.25% solution of claimed modification of the compound in 0.9% aqueous solution of NaCl | 7 | 61.6 ± 6.3 | 89.0 ± 4.9 | 95.4 ± 3.8 |

TABLE 5

The results of comparative assessment of plane wounds treatment with the known crystalline form and the claimed modification of the said compound

| Series No.<br>1 | No. of animals<br>2 | Mean time of falling off of crusts, days<br>3 | Mean time of healing, days<br>4 | Speeding up of healing, %<br>5 |
|---|---|---|---|---|
| 1<br>0.9% aqueous solution of NaCl - control | 6 | 11.0 ± 0.9 | 24.0 ± 1.9 | — |
| 2<br>1% solution of the known crystalline form of the said compound in 0.9% aqueous solution of NaCl | 7 | 9.6 ± 0.5 | 18.4 ± 1.6 | 23.3 |

TABLE 5-continued

The results of comparative assessment of plane wounds treatment with the known crystalline form and the claimed modification of the said compound

| Series No.<br>1 | No. of animals<br>2 | Mean time of falling off of crusts, days<br>3 | Mean time of healing, days<br>4 | Speeding up of healing, %<br>5 |
|---|---|---|---|---|
| 3<br>0.25% solution of the claimed modification in 0.9% aqueous solution of NaCl | 7 | 8.6 ± 0.7 | 17.7 ± 1.6 | 26.2 |

The analysis of the results presented in Tables 3, 4 and 5 demonstrated that the use of a 4-fold lower dose of the claimed modification of the said compound as compared with the dose of the known form of the compound markedly speeded up the healing of both linear and plane wounds. The rupture strength of linear wounds at 7 days increased by 90.4% as compared with the control and by 43% as compared with the use of the know form of the compound. The time of complete healing of plane wounds shortened by 26.2% as compared with the control and by 12% as compared with the known form of the compound.

Thus, the claimed crystalline modification 2,4-dioxo-6-methyl-1,2,3,4-tetrahydropyrimidine manifests increased wound-healing activity which permits to reduce considerably the dosage of the pharmaceutical based thereon achieving an increased therapeutic effectiveness.

Trials of the toxicity of the claimed crystalline modification of the said compound were carried out comparing it with the known crystalline form of the said compound.

Investigations of the general toxic effect of the claimed crystalline modification of 2,4-dioxo-6-methyl-1,2,3,4-tetrahydropyrimidine and the known crystalline form of the said compound were carried out in 3 rodent species (random-bred white mice, rats, and chinchilla rabbits).

The results obtained in the studies of the acute toxicity permit to classify the claimed modification in the Vth class of toxicity (practically non-toxic compounds) according to the generally accepted classification. The known crystalline form of the said compound has slightly higher toxicity, although they belong to the same group. According to the data obtained by the tests of acute toxicity by the intraperitoneal route, the claimed modification of the said compound may be allocated to the VI class of relatively harmless compounds.

Since its mean lethal dose could not be established by the subconjunctival route of inoculation, by the date of acute toxicity it is impossible to assess objectively the danger of dermato-resorptive effect.

After subacute routes of inoculation, the death of the animals was not marked, and the cumulative effect was weak.

The study on the safety of long-term subconjunctival inoculations of the claimed modification in comparison with the known form of the said compound was carried out in a 2-month-long toxicological experiment in 148 mature male and female white rats and 49 male and female chinchilla rabbits.

Male rats and rabbits were given subconjunctivally I drop each of 2%, 25% and 50% suspension of the claimed modification of the said compound into each eye once daily.

The results obtained were compared with those in a group of male rats and rabbits given one drop of 2% suspension of the known form of the said compound into the eye. Besides, a 2% suspension of the claimed modification of the said compound was given to a group of female rats and rabbits which were compared with the control group. In a separate series of experiments in the same animals (rats, rabbits) carried out by the same schedule of a chronic experiment, the effect of the claimed pharmaceutical in the form of an eye ointment containing as the active substance the claimed modification of the said compound was determined. The results of this study confirm the data obtained in the studies of the effect of the claimed compound. Comparisons with the pharmaceutical containing the known form of the said compound gave analogous results.

A long-term administration of the compound under study and of the pharmaceutical produced no macroscopic local inflammatory reactions of the eyes. Microscopic examinations, however, revealed changes in distal parts of the eye. Under the influence of large doses of the compound under study lymphoid infiltrates were formed in the ciliary body, iris, and sometimes in the initial parts of the optic nerve, but these changes were reversible.

The use of 2% suspensions and an eye ointment on the basis of the claimed and the known forms of the said compound caused a minimal reactive effect within 1 month of treatment, which slightly increased after 2 months of treatment but was completely reversible after the treatment had been discontinued. The therapeutic scope of the claimed modification is sufficient. The ratio between a therapeutic dose and that causing irreversible changes is 1:25.

The studies of the allergenic and immunotoxic properties of the claimed crystalline modification of the said compound and the medicinal preparation based thereon showed the claimed compound and the preparation to produce no specific reaction of leukocyte agglomeration, no specific leukocyte lysis, to exert no effect on the functional activity of the B-cell immunity, not to inhibit the functional activity of the Te-cell immunity, not to be conducive to the formation of the tumor necrosis factor. Thus, the results of the trials showed the claimed compound and the medicinal preparation based thereon possessed no allergenic and immunotoxic properties.

The claimed crystalline modification of 2,4-dioxo-6-methyl-1,2,3,4-tetrahydropyrimidine, according to the invention, is an active substance of a medicinal preparation which has antiinflammatory and wound-healing effect.

The claimed medicinal preparation may be used in any pharmaceutically acceptable medicinal form (powder, liniment, suspension, ointment, and others).

The claimed medicinal preparation in the suspension form has a high wound-healing activity and manifests an unexpected effect of prolonged action. The medicinal preparation in the suspension form preferably contains 1.0–2.5% by weight of the active substance.

The choice of the concentration of the active substance is due to the fact that in the said range of concentrations a high therapeutic effect is observed without any side effects.

The use of a pharmaceutical diluent of doubly-distilled water for injections of 0.9% sodium chloride aqueous solution is due to the fact that only the combination of the active substance with one of the said diluents is conductive to the development of the prolonging effect of the active substance.

A suspension is prepared by mixing the ingredients resulting in creation of disperse-heterogenous system wherein the disperse phase in the active substance and the dispersion medium is the doubly-distilled water for injections or 0.9% NaCl aqueous solution.

The authors established that the active substance in the suspension manifests a prolonging effect.

The following trials were carried out to prove the prolonging effect. The rate of dissolution of the active substance is determined in a "rotary basket" type DT-D6 apparatus (Erweka Co, BRD) at a mixing rate of 50 rpm. The dissolving medium is water for injections in a volume of 1000 ml at a temperature of 37±1° C. The content of the active substance in the solution is determined spectrophotometrically in a spectrophotometr No. 75 (Perkin-Elmer Co) at a wave length of 259 nm. For comparison, the known crystalline form of the said compound is used under identical conditions. The parameter for comparison is the constant of dissolution rate based on the mean results of the compound transition into solution from the amount thereof used (0.25 g) in the time of 0 to 45 min. The water for injections is used as a control.

The results of the trials showed a high constant of the dissolution rate of the known crystalline form of the said compound ($K=0.18$ $min^{-1}$) and a marked prolonged dissolution of the claimed crystalline modification of the said compound with the $K=0.025$ $min^{-1}$.

The sedimentation stability of the claimed preparation in the form of 2% suspension was studied by the photoelectrocolorimetric method. For comparison, 2% aqueous suspension of the known crystalline form of the said compound was studied. Analysis of the obtained results indicated that the 2% suspension of the claimed crystalline modification had good stability and retained homogeneity for 2 hours. A suspension of the known crystalline form of the said compound had practically no sedimentation stability, its optic density decreasing markedly within 5 minutes.

The optimality of the chosed concentrations of the active substance in the claimed preparation in the suspension form has been confirmed by clinical experimental studies.

Thus, it was demonstrated that a decrease in the concentration of the active susbtance in suspension resulted in lower therapeutic effects in eye burns and development of complications. In a group of animals treated with 0.5% suspension of the active substance, corneal perforation occurred in 8% of the cases and in some cases intensive keratoleukomas developed. An increase in the suspension concentration to 3% did not enhance the therapeutic effect but caused irritation of the eye ball in 78% or rabbits.

Thus, the highest therapeutic effect without side effects was found to be achieved with suspensions containing from 1.0 to 2.5% by weight of the active substance.

The selected pharmaceutical diluent—0.9% NaCl aqueous solution or water for injections is conducive to achieving the prolongation effect of the active substance.

The therapeutic efficacy of the claimed preparation in the suspension form was assessed in medico-biological studies on the model of chemical eye burn in rabbits.

Alkaline burns of the 3rd degree in both eyes were produced by introduction of 3 drop of 5% sodium hydroxide solution into the conjunctival sac with the exposure of 17 seconds followed by washing with water. The degree of the burn was determined within 3 hours, and then the treatment started consisting of subconjunctival administration twice daily of the claimed preparation in the form of sterile suspension with the active susbtance concentrations of 2.5% by weight, 1% by weight, 0.5% by weight (for comparison). The clinical course of the burn was evaluated under control of 1% aqueous solution of methylene blue. The efficacy of the treatment was assessed by the results of histological examinations. For this purpose, the corneal tissue was fixed in 1% neutral formalin followed by embedding into paraffin. The sections were stained with hematoxylin-eosin.

Three groups of animals were treated, each group consisting of 24 rabbits (48 eyes). The first group of animals was treated with 2.5% suspension of the active substance in 0.9% NaCl aqueous solution and in the water for injections which was administered subconjunctially twice daily.

The animals were sacrificed by air embolism at 1, 3, 5, 7, 10, 14, 21 and 28 days after the beginning of the treatment. The efficacy of treatment was evaluated by the clinical picture of the course of eye burn and the results of histological and histochemical studies. The results showed that as early as by the 3rd day epithelization of the greater part of the cornea occured in the animals of the study groups. The epithelium, however, was thin (1–2 layers of epitheliocytes). In the underlying tissue with proliferating fibrillar connective tissue there were many macrophages, eosinophilic leukocytes, neutrophils, lymphocytes and penetrating hemocapillaries. The main substance of the cornea was disorganized, there were areas of thinning of the substantia proper. Accumulation of all kinds of leukocytes was observed in the anterior chamber of the eyes. At 5 days, the burn site was mostly epithelized by multilayer epithelium. Some of epitheliocytes were vacuolated. The proper substance of the cornea at the site of the burn was injected with small blood vessels and infiltrated with mononuclear and polynuclear leukocytes. At 7 days areas of epithelium were more extended, mostly multilayered and uneven. In the underlying connective tissue infiltrated with mononuclear leukocytes, larger blood vessels were penetrating. In 2 weeks, the defects of the epithelium were insignificant, infiltration with mononuclear leukocytes, proliferation of fibrillar connective tissue and penetration of the blood vessels decreased considerably. The regenerating epithelium had 2–3 layers. By 18 days epithelization of the cornea was completed. The epithelium covering the burn surface was markedly multilayered and penetrated with blood vessels.

The second group of animals was treated with 1.0% suspension of the active substance in 0.9% aqueous solution of NaCl and in water for injections.

The results showed that as early as by the 3rd day, epithelization of the most part of the cornea occurred in the animals of this group. The epithelium, however, was thin. The main substance of the cornea was disorganized, showing areas of thinning of the substantia proper. Accumulation of leukocytes was observed in the anterior chamber of the eye.

At 7 days the site of the burn was mostly epithelized with multilayered epithelium, some of epitheliocytes were vacuolated. The proper substance of the cornea at the site of the burn was injected with small blood vessels and infiltrated with mononuclear and polynuclear leukocytes.

At 18 days the defects of the epithelium were insignificant, the regenerating epithelium had 2–3 layers. By 21 days, epithelization of the cornea completed.

For treatment of the third group of animals 0.5% suspension of the active substance (a comparative version) was used.

In this study group, on the 3rd day of observation the discharge was moderate, mucous; the defect of the corneal epithelium was not deep, there appeared areas of newly formed epithelium. In subsequent periods of observation the discharge remained moderate, mue cous,necrotic areas of the conjunctiva decreased in size, the layer of newly formed epithelium increased. By 10 days, occasional newly formed blood vessels appeared in the periphery of the cornea. In 4 eyes, however, the course of the burn was more severe, a secondary infection appeared. The discharge was mucopurulent, the corneal infiltration was observed, and purrulent exudate into the anterior chamber appeared. By 10 days, in these eyes there occured perforation of the cornea. In the other eyes the course of the process was favourable. The defect of the corneal epithelium continued to decrease and by 21 days was practically absent; on its site keratoleukomas of different intensities formed. By 28 days, clearing of the cornea in the periphery and keratoleukoma of low intensity in the center were observed in 5 eyes.

The results of the experimental studies are presented in Table 6. The analysis of the experimental data showed that administration of the claimed preparation twice daily in the suspension form in cases of eye burns resulted in complete restoration of the epithelium by 18–20 days, without any side effects and complications. A special feature of the pharmacological action of the suspension consists in early vascularization of the site of lesion which positively affects the time course of the wound healing and enhances the antiinflammatory effect of the preparation. At the same time, if compared with the eye ointment, the claimed suspension has a preferable regimen of administration (twice daily, whereas the eye ointment is applied 6 times daily) which is due to the prolonged therapeutic effect thereof.

TABLE 6

Comparative evaluation of treatment of alkaline eye burns using different concentrations of the active substance in the claimed preparation used in the form of a suspension (%)

| Animal groups | | Epithelization of the cornea Beginning (days) | | | |
|---|---|---|---|---|---|
| | | 1–2 | 3–4 | 5–7 | 8–10 |
| 1 | Control (no treatment) (30 eyes) | — | — | — | — |
| 2 | Treatment with 0.5% suspension of the active substance (48 eyes) | — | 48.2 | 28.4 | 23.4 |
| 3 | Treatment with 1.0% suspension of the active substance (48 eyes) | — | 68.8 | 31.2 | — |
| 4 | Treatment with 2.5% suspension of the active substance (48 eyes) | — | 75.4 | 24.6 | — |

| Animal groups | Epithelization of the cornea Completion (days) | | | | | Vascularization of the cornea Beginning (days) | | |
|---|---|---|---|---|---|---|---|---|
| | 5–7 | 14–17 | 18–20 | 28 | Frequency | 5–7 | 8–10 | 11–14 |
| 1 | — | — | — | — | 89.3 | — | 89.3 | — |
| 2 | — | 2.5 | 48.6 | 40.6 | 68.4 | — | 15.7 | 52.7 |
| 3 | 38.2 | 41.5 | 20.3 | — | 68.0 | — | 13.7 | 54.3 |
| 4 | 41.6 | 58.4 | — | — | 68.6 | — | 13.2 | 55.4 |

| Animal groups | Corneal infiltration | Hypopyon | Increase of intraocular pressure | Cornea perforation | Loss of the eye | Outcomes Large intensive corneal leukoma | Keratoleukoma |
|---|---|---|---|---|---|---|---|
| 1 | 100 | 76.6 | 89.7 | 100 | — | — | — |
| 2 | 17.6 | 8.3 | 7.6 | 8.3 | 8.3 | 34.8 | 46.5 |
| 3 | 14.0 | 6.2 | 6.2 | — | — | — | 10.2 |
| 4 | 12.5 | 4.1 | 4.1 | — | — | — | 6.2 |

The claimed medicinal preparation in the form of liniment, according to the invention, preferably contains 5% by weight of the active substance. As a pharmaceutical solvent for the claimed liniment, any acceptable emulsion base may be used, for example, sunflower seed oil, see buckthorn oil, or castor oil and others. For the claimed liniment, preferably castor oil is used which facilitates complete and rapid release of the active substance.

The evaluation of the therapeutic efficacy of the claimed liniment was done experimentally in rats in which aseptic inflammation of the vaginal mucosa (ulcers) was induced by treatment of the vagina with 7% solution of silver nitrate with the exposure of 3 minutes. The efficacy of treatment was evaluated visually and by histological examinations. For this purpose the vaginal tissue was fixed in 10% neutral formalin followed by embedding into paraffin. The sections were stained with hematoxylin-eosin.

Three series of experiments were carried out using 24 animals in each series: 1 series—intact control. In this group, after the induction of the burn and formation of an extensive ulcer (80% of the mucosa surface), the vaginas of the rats were treated daily for 20 days with a swab wetted with distilled water; the 2nd series—a comparative control—24 hours after the burn, when an ulcer formed, the vaginas of the rats were treated daily for 20 days with a swab wetted with sea buckthorn oil. The sea buckthorn oil was chosen as a comparative control because it was found to be effective in treatment of torpid processes, for instance, trophic ulcers; the 3rd series—treatment using the claimed liniment containing 4% by weight and 6% by weight of the active substance.

In this group, 24 hours after inflicting the burn and daily for 20 days the vaginas of the rats were treated with the claimed liniment containing the above-said amount of the active substance. At 5, 10, 15 and 20 days 6 animals from each series were sacrificed and the condition of the vaginal mucosa was studied visually using staining of the affected areas of the mucosa with methylene blue solution. The results were evaluated as follows:

+++—total burn (inflammation) of the entire surface or considerable areas of deep lesions with signs of necrosis and dense infiltration occupying over 80% of the surface;

++—moderately severe lesions without infiltrations and necroses occupying about 50% of the surface;

+—a mild inflammatory reaction in areas occupying less than 50% of the surface;

0—normal mucosa of intact rats.

Visual examinations of the animals in the first series revealed at 24 hours after treatment of the vaginal mucosa with silver nitrate that the surface of the burn comprised 80% of the total mucosa surface, had foci of deep lesions such as ulcerations, detachment of epithelium, necrosis. At 5 days the pattern of the lesions did not change significantly. At 10–15 days the areas of deep lesions diminished down to 60%. At 20 days the condition of mucosa was close to normal, the stained surface did not exceed 20%, the number of deep foci of lesions was insignificant.

Pathomorphological studies showed that within 24 hours after inflicting of the burn extensive necroses of the epithelium and underlying connective tissue could be determined histologically. The zone of necrosis was surrounded by leukocyte inflammatory torus beyond which was a zone of extensive edema and defibrillation of the connective tissue with stagnation of blood vessels and hemorrhages. At 5 days the depth of the lesion increased and the leukocyte torus extended. The number of blood vessels in stasis increased. The edema of the surrounding tissues decreased slightly.

Within 10 days the pattern of lesions was the same. At 15 days, the excrescence of the epithelium on the wound surface was observed as well as a decrease of the leukocyte torus in which the number of blood vessels increased. At 20 days there were no foci of necrosis, the area of non-epithelized foci was insignificant. The leukocyte reaction was practically absent as well as the stasis of the blood vessels and edema of the surrounding tissues.

By the results of visual observations of the animals in the 2nd experimental series (the use of sea buckthorn oil), the area of staining decreased markedly by the 5th day. By 15 days, the mucous membrane recovered practically completely.

Pathomorphological studies showed at 5 days extensive foci of necrosis with a strong leukocyte torus, extensive edema of the surrounding tissues, stasis of the blood vessels.

At 15 days, the areas of necrosis decreased significantly, the inflammatory leukocyte torus decreased as well.

At 20 days, almost complete epithelization of the wound surface was observed, leukocyte infiltration was insignificant, the edema persisted, the vessels distended.

According to the visual observations of the animals of the 3rd series (use of the claimed liniment), at 5 days after the burn there were practically no deep lesions, and the area of staining decreased considerably (to 20–30%). By 10 days, the vaginal mucosa recovered practically completely.

TABLE 7

Comparative dynamics of reparative regeneration in aseptic inflammation in rats treated with the claimed liniment and sea buckthorn oil

| Days of examination | claimed liniment | | sea buck- thorn oil | Intact animals |
|---|---|---|---|---|
| | 4% by weight of the substance | 6% by weight active | | |
| 24 hours | +++ | +++ | +++ | +++ |
| 5 days | ++ | ++ | ++ | +++ |
| 10 days | + | + | ++ | ++ |
| 15 days | 0 | 0 | + | ++ |
| 20 days | 0 | 0 | + | + |

According to pathomorphological examinations, at 10 days no foci of necrosis could be detected, epithelization of the wound surface occurred against the background of insignificant leukocyte infiltration. At 20 days complete regeneration of the epithelial tissue was observed. Comparative dynamics of reparative regeneration observed in the studies is presented in Table 7.

It will be seen in the Table that the claimed liniment showed the highest regenerating activity. As early as 5 days the lesion was decreased to 30% of the initial area (in some areas to 50%), and at 10 days the vaginal mucosa was almost completely restored.

Thus, the experimental results show the claimed liniment to possess high regenerative, antiinflammatory and wound-healing activities. The regenerative activity is manifested in burns of the III—IV degrees when, because of the lack of epithelial elements, the maturation of the granulating tissue is delayed and there forms a granulation torus preventing the manifestation of the regenerative capacity of the epithelium. The claimed liniment also decreases the exudative-alternative changes in the focus of lesion, prevents excessive formation and outgrowth of the connective tissue and development of scars.

At the same time, biopharmaceutical studies revealed complete conformity of the claimed liniment to the standard requirements and high bioaccessibility exceeding that of the known ointment by 30-fold.

The claimed preparation can also be used in the ointment form. According to the invention, the claimed preparation in the form of an ointment preferably contains 1.0–2.5% by weight of the active substance, and as a pharmaceutical diluent it contains an ointment basis consisting of a mixture of lanolin and vaselin in a ratio of 1.0:1.0–2.5.

The choice of the active substance concentration is determined by the fact that in indicated range of concentrations it shows a high therapeutic effect not accompanied by side effects.

The use of lanolin and vaselin mixture as the preferable ointment basis is due to the fact that the said mixture is conducive to most rapid penetration of the active substance into the wound surface. The choice of the quantitative ratio of this mixture is conditioned by the fact that with the said range the highest effect of release of the active substance from the ointment is observed.

The claimed ointment exhibits a high antiinflammatory and wound-healing activity in treatment of burns and wounds of different origin. In particular, the claimed ointment is highly effective in ophthalmological practice in treatment of burns and wounds of the eyes. The effectiveness of the claimed ointment in comparison with that of the ointment wherein the active substance is the known crystalline form of the said compound was studied experimentally for treatment of eye burns in rabbits. The experiments were carried out in chinchilla rabbits aged about 6 months and weighing 2.0–2.5 kg.

Alkaline burns of the eyes of the 3rd degree were inflicted by administration of 3 drops of 5% sodium hydroxide solution (exposure for 17 sec.) into the conjunctival sac; then the eye was washed with water. The degree of the burn was determined in 3 hours after which the treatment started.

The 1st series of animals (three groups) was treated with the claimed eye ointment containing 1% by weight, 2% by weight and 2.5% by weight of the active substance; the 2nd series of animals (one group) was treated with the known ointment containing 2% by weight of the active substance; the 3rd series (1 group) was control.

The ointment was placed into the conjunctival sac 6 times daily for 28 days. In all the groups the treatment was combined with preliminary washing of the eyes with 0.02% solution of nitrofurazone. Each group had 24 rabbits (48 eyes).

The animals were sacrificed by aeroembolism at 1, 3, 5, 7, 10, 14, 21 and 28 days after the beginning of the treatment. The efficacy of the treatment was evaluated by the pattern of the clinical course of the eye burn and the results of histological and histochemical studies. For histological examinations, the corneal tissue was fixed in 10% formalin solution followed by embedding into paraffin. Corneal sections were stained with hematoxylin-eosin and PAS reagent for mucopolysaccharides. The results of the experiment are presented in Table 8.

TABLE 8

Comparative assessment of the efficacy of the claimed and known ointment in treatment of eye burns

| No. of Preparation | eyes (100%) | Epithelization of eye cornea in % of the total number of eyes Beginning at days | | | |
|---|---|---|---|---|---|
| | | 1–2 | 3–4 | 5–7 | 8–10 |
| 1 The claimed ointment containing 1% by weight of the active substance | 48 | 65.2 | 19.4 | 15.4 | — |
| 2 The claimed ointment containing 2% by weight of the active substance | 48 | 72.9 | 18.8 | 8.3 | — |
| 3 The claimed ointment containing 2.5% by weight of the active substance | 48 | 72.9 | 17.4 | 9.5 | — |
| 4 The known ointment | 48 | — | 50 | 12.5 | 37.5 |
| 5 No treatment (control) | 48 | — | — | — | — |

| | Epithelization of the eye cornea in % of the total number of eyes completion at days | | | | Lack of complete epithelization at 28 days in % of total number of eyes |
|---|---|---|---|---|---|
| | 3 | 5–7 | 14–17 | 13–20 | 28 |
| 1 | 6.7 | 17.9 | 48.8 | 26.6 | — | — |
| 2 | 8.3 | 18.7 | 51.8 | 21.2 | — | — |
| 3 | 9.2 | 21.3 | 50.6 | 18.9 | — | — |
| 4 | — | — | — | 33.4 | 29.2 | 37.5 |
| 5 | — | — | — | — | — | 100 |

| | Vascularization of cornea in % of total number of eyes | | | |
|---|---|---|---|---|
| Frequency | | Beginning at days | | |
| | | 5–7 | 8–10 | 11–14 |
| 1 | | — | — | — |
| 2 | 45.8 | 25.9 | 19.9 | — |
| 3 | — | — | — | — |
| 4 | 82.5 | — | 58.3 | 24.2 |
| 5 | 89.3 | — | 89.3 | — |

| | | | | | Outcomes in % of the total no. of eyes | |
|---|---|---|---|---|---|---|
| | Corneal infiltration, % | Hypopyon, % | Increased intraocular pressure | Symblepharon, % | gross intensive corneal leukkoma | moderately intensive keratoleukoma |
| | 1 | 2 | 3 | 4 | 5 | 6 |
| 1 | 10.2 | 11.6 | 11.3 | — | — | 9.8 |
| 2 | 8.3 | 10.4 | 10.4 | — | — | 8.3 |
| 3 | 8.3 | 9.8 | 9.8 | — | — | 8.3 |
| 4 | 66.6 | 62.7 | 62.7 | 16.6 | 45.3 | 21.3 |
| 5 | 100 | 76.6 | 89.7 | 66.6 | 100 | — |

As will be seen from the results in Table 8, in treatment with the claimed ointment areas of newly formed corneal epithelium appeared as early as the first day and by 20 days complete epithelization of the cornea occurred. Treatment with the known ointment was of low efficacy: even within 28 days 70.8% of the eyes had no complete epithelization of the cornea and some defects of the epithelium were still present. As compared with the known ointment, the claimed ointment has strong regenerative properties inducing not only much earlier beginning of the corneal epithelization but also most rapid recovery of the entire epithelial layer, corneal transparency of the cornea, and the normal histological structure thereof.

It may be seen in Table 8 that after treatment with the known ointment in 45% of the eyes there develops gross intensive corneal leukoma and in 21% moderately intensive keratoleukoma. In treatment with the claimed ointment keratoleukoma of moderate intensity developed only in 8.3–9.8% of the eyes.

In treatment with the claimed ointment, there were practically no instances of secondary infection as shown by the low percentage of the eyes with corneal infiltration (8.3–10.2%). Thus, it may be concluded that in treatment of the eye burns with the claimed ointment no secondary infection of the wound practically occurs. At the same time, in treatment with the known ointment, as seen in Table 8, there were cases of secondary infection as indicated by the development of corneal infiltration in 66.6% of the eyes.

The antiinflammatory property of the claimed ointment in treatment of eye burns was confirmed by the fact that signs of toxic uveitis were very weak and observed only in 10.4% of the cases exerting no effect on the outcome of the treatment.

When the known ointment was used, signs of toxic uveitis with a stripe of hypopyon on the bottom of the anterior chamber and increased intraocular pressure were observed in 62.7% of the cases indicating the development of an intensive inflammatory process.

Thus, the above-described trials provide the evidence that the claimed ointment reduced the inflammatory process and secondary infection when used for treatment of the eye burns and facilitated early corneal epithelization by strong stimulation of the regeneration processes as a result of which transparency of the cornea was restored.

For treatment of poorly healing infected wounds it is expedient to use the claimed medicinal preparation consisting of the new crystalline modification of 2,4-dioxo-6-methyl-1,2,3,4-tetrahydropyrimidine in combination with para-aminobenzolsulphamide at the following ratio thereof in % by weight:

| | |
|---|---|
| the crystalline modification of 2,4-dioxo--6-methyl-1,2,3,4-tetrahydropyrimidine | 45–55, |
| para-aminobenzolsulphamide | 45-55. |

The efficacy of the claimed preparation was tested clinically in most severe cases of poorly healing suppurative wounds of various nosological forms (trophic ulcers of venous origin of small/under 5 cm$^2$/and large/over 5 cm$^2$/ sizes and postoperative suppurative wounds).

The following features were taken into account: decrease of the inflammatory reaction, the time of cleaning of the wounds, the intensity of granulation growth, marginal epithelization. For purposes of comparison, the treatment was carried out in parallel using the known ointment containing 10% by weight of the active substance—the known crystalline form of 2,4-dioxo-6-methyl-1,2,3,4-tetrahydropyrimidine.

In trophic ulcers of venous origin the use of the claimed preparation led to significant decrease of the inflammatory reaction within the first two days, intensively stimulated the growth of granulations and induced rapid epithelization. Ulcers of 2 cm in diameter healed with in 7–10 days (the usual time of treatment 14–18 days). The postoperative suppurative wounds of 4 to 20 cm$^2$ in size treated with the claimed preparation cleared rapidly, the redness and inflammatory infiltration on the wound edges decreased and disappeared, the pains subsided within 2–3 days, the granulations bright and fine-grained. The period of healing was shortened by 2-fold. The results of the trails are presented in Tables 9 and 10.

TABLE 9

The average periods of treatment (days) of wounds using the claimed and known medicinal preparations

| | Time of treatment days | |
|---|---|---|
| Nosological form of the wounds | using the claimed preparation | the known ointment |
| Trophic ulcer of venous origin, the area less than 5 cm$^2$ | 9 | 16 |
| Trophic ulcer of venous origin, the area more than 5 cm$^2$ | 18 | 35 |
| Suppurative postoperational wounds | 8 | 15 |

TABLE 10

The results of treatment of wounds using the claimed preparation as compared with the known ointment

| | | The results of treatment with | | | |
|---|---|---|---|---|---|
| | | the claimed preparation | | the known ointment | |
| Nosological form of wounds | No. of patients | improvement | no improvement | improvement | no improvement |
| Trophic ulcers of venous origin | 12 | 6 | — | 3 | 3 |
| Supparative post-operational wouns | 12 | 6 | | 4 | 2 |

According to the invention, the active substance, a new crystalline modification of 2,4-dioxo-6-methyl-1,2,3,4-tetrahydropyrimidine is prepared by cooling a solution of 2,4-dioxo-6-methyl-1,2,3,4-tetrahydropyrimidine in water or an organic solvent or in a mixture thereof with a cooling agent at a rate not below 6° C./min. to its complete crystallization followed by separation of the resulting crystals and drying thereof. The cooling agent may be any substance capable of decreasing the temperature of the substance to be cooled at a rate below 6° C./min. The optimal substance used as a cooling agent is liquid nitrogen or liquid carbon dioxide the use of which increases the yield of the target product due to the rapid establishment and further maintenance of the necessary rate of cooling.

The new crystalline modification of the said compound is obtained at a rate of cooling not below 6° C./min; carrying out the process of cooling at a rate below 6° C./min does not produce the new crystalline modification. The upper range of the rate of cooling is not limited. The new crystalline modification is formed at any maximally achievable rate of cooling of the initial solution. The process of cooling is carried out in water or any organic solvent, or in the mixture thereof in which the initial substance is soluble. The preferable solvents in which the initial substance dissolves well are water and ethanol. With then, the highest yield of the target product is achieved. The claimed substnce may be obtained irrespectively of the concentration of the initial substance in the solution. The choice of the condition of drying at a pressure not above $10^{-2}$ mm Hg is due to the requirement that the final dried product must have humidity not exceeding 3%. Drying at a pressure above $10^{-2}$ mm Hg results in obtaining a wet, spreading unstable mass.

For better understanding of the present invention, the following examples of preparation of the claimed substance are presented.

EXAMPLE 1

1.5 l of aqueous solution of 2,4-dioxo-6-methyl-1,2,3,4-tetrahydropyrimidine with a concentration of 20 g/l is cooled with liquid nitrogen at a rate of cooling 6° C./min to complete crystallization thereof. The resulting frozen mass is placed on trays and placed into a freeze drier. The drying is carried out at a pressure of $10^{-2}$ mm Hg to the residual humidity of 3%. The yield of the target product is 300 g (100%). The resulting product is a white powder with high fluidity. The resulting substance is characterized by values of interplane spacings d and relative reflexes I coinciding with the respective above-presented values of the new crystalline modification of 2,4-dioxo-6-methyl-1,2,3,4-tetrahydropyrimidine. By all the characteristics (NMR, IR-, KR-spectra) the obtained substance corresponds to the claimed new crystalline modification of the said substance.

EXAMPLE 2

The process is carried out as described in Example 1, using 500 ml of the solution of the initial substance in the water-ethanol mixture (1:1), with a concentration of 20 g/l. The yield of the target product is 96% by weight. The resulting substance has the characteristics analogous to those of Example 1.

EXAMPLE 3

The process is carried out as described in Example 1 with the rate of cooling 30° C./min. The yield of the target product is 98.2% by weight. The resulting substance has the characteristics analogous to those of Example 1.

EXAMPLE 4

1.5 l of ethanol solution of 2,4-dioxo-6-methyl-1,2,3,4-tetrahydropyrimidine at a concentration of 10 g/l is cooled with liquid nitrogen at a rate of 8° C./min to complete crystallization of the solution. The resulting frozen mass in put into drier. The drying is carried out at a pressure of $10^{-5}$ mm Hg. The yield of the target product is 95.6% by weight. The resulting substance has the characteristics analogous to those of Example 1.

EXAMPLE 5

The process is carried out as described in Example 1, at a concentration of the initial substance in ethanol of 10 g/l, and the cooling agent is carbon dioxide. The yield of the target product is 96.8% by weight. The resulting substance has the characteristics analogous to those of Example 1.

INDUSTRIAL APPLICATION

The claimed new crystalline modification of 2,4-dioxo-6-methyl-1,2,3,4-tetrahydropyrimidine has the antiinflammatory and wound-healing activity and finds application as the active substance of a medicinal drug for treatment of wounds and burns of different origin, in particular, in ophthalmological practice for treatment of eye burns and wound damages. Besides, the claimed preparation is used for treatment of poorly healing infected wounds (trophic ulcers of venous origin, postoperative suppurating wounds).

What is claimed is:

1. A crystalline modification of 2,4-dioxo-6-methyl-1,2,3,4-tetrahydropyrimidine characterized by the following interplane spacings d and relative intensity of reflexes I:

| d, Å | I |
| --- | --- |
| 9.668 | 9 |
| 6.592 | 100 |
| 4.838 | 36 |
| 3.843 | 5 |
| 3.625 | 7 |
| 3.431 | 20 |
| 3.248 | 48 |
| 2.916 | 8 |
| 2.799 | 9 |
| 2.479 | 4 |
| 2.429 | 7 |
| 2.405 | 6 |
| 2.292 | 8 |
| 2.043 | 4 |
| 1.699 | 3 |

2. A process for preparation of a crystalline modification 2,4-dioxo-6-methyl-1,2,3,4-tetrahydropyrimidine of claim 1 comprising cooling a solution of 2,4-dioxo-6-methyl-1,2,3,4-tetrahydropyrimidine in water, in an organic solvent, or in a mixture thereof using a cooling agent at a rate not below 6° C./min until the solution has substantially completely crystallized to form crystals, then isolating and drying the crystals.

3. A process according to claim 2 wherein ethanol is used as an organic solvent.

4. A process according to claim 2 wherein the cooling agent used is liquid nitrogen or liquid carbon dioxide.

5. The process according to claim 2, wherein the drying is carried out under vacuum at a pressure not below $10^{-2}$ mm Hg.

6. The process according to claim 4, wherein the drying is carried out under vacuum at a pressure not below $10^{-2}$ mm Hg.

7. A pharmaceutical preparation with anti-inflammatory and wound-healing effects comprising an active substance and a pharmaceutically acceptable carrier or diluent wherein the active substance is the crystalline modification of 2,4-dioxo-6-methyl-1,2,3,4-tetrahydropyrimidine of claim 1.

8. A pharmaceutical preparation according to claim 7 in suspension form containing 1.0–2.5% by weight of the active substance.

9. A pharmaceutical preparation according to claim 7 in suspension form wherein the pharmaceutically acceptable diluent is 0.9% aqueous solution of sodium chloride or double distilled water.

10. A pharmaceutical preparation according to claim 7 which is a liniment containing the active substance in an amount of 4–6% by weight.

11. A pharmaceutical preparation according to claim 7 which is a liniment wherein the pharmaceutically acceptable diluent is castor oil.

12. A pharmaceutical preparation according to claim 7 which is an ointment containing the active substance in an amount of 1.0–2.5% by weight.

13. A pharmaceutical preparation according to claim 7 which is an ointment wherein the pharmaceutical diluent is an ointment base comprising of a mixture of lanolin and petroleum jelly in a ratio of 1.0:1.0–2.5, respectively.

14. A pharmaceutical preparation with antiinflammatory and wound-healing effect comprising the crystalline modification of 2,4-dioxo-6-methyl-1,2,3,4-tetrahydropyrimidine according to claim 1 and para-aminobenzolsulphamide at the following ration in % by weight:

| | |
|---|---|
| the crystalline modification of 2,4-dioxo--6-methyl-1,2,3,4-tetrahydropyrimidine | 45–55 |
| para-aminobenzolsulphamide | 45-55. |

\* \* \* \* \*